(12) United States Patent
Sayre

(10) Patent No.: US 9,775,737 B2
(45) Date of Patent: Oct. 3, 2017

(54) FINGER TRIGGER SPLINT FOR JOINT IMMOBILIZATION AND FLEXION INHIBITION

(71) Applicant: Serenity Sayre, Danville, CA (US)

(72) Inventor: Serenity Sayre, Danville, CA (US)

( * ) Notice: Subject to any disclaimer, the term of this patent is extended or adjusted under 35 U.S.C. 154(b) by 0 days.

(21) Appl. No.: 15/368,875

(22) Filed: Dec. 5, 2016

(65) Prior Publication Data

US 2017/0079831 A1 Mar. 23, 2017

Related U.S. Application Data

(63) Continuation of application No. 14/721,900, filed on May 26, 2015.

(51) Int. Cl.
A61F 5/058 (2006.01)
A61F 5/10 (2006.01)
A61F 5/01 (2006.01)

(52) U.S. Cl.
CPC ...... *A61F 5/05875* (2013.01); *A61F 5/05825* (2013.01); *A61F 5/10* (2013.01); *A61F 5/0118* (2013.01)

(58) Field of Classification Search
CPC .. A61F 5/00; A61F 5/01; A61F 5/0118; A61F 5/013; A61F 5/04; A61F 5/05; A61F 5/058; A61F 5/05825; A61F 5/05866; A61F 5/05875; A61F 5/10
USPC .......................................................... 602/22
See application file for complete search history.

(56) References Cited

U.S. PATENT DOCUMENTS

| | | | |
|---|---|---|---|
| 1,471,948 A | 10/1923 | Claude | |
| 1,837,691 A | 12/1931 | Thigpen | |
| 4,103,682 A | 8/1978 | Franzl | |
| 5,346,462 A * | 9/1994 | Barber | A61F 5/05875 128/880 |
| 6,261,253 B1 * | 7/2001 | Katzin | A61F 5/0118 602/12 |
| 6,478,761 B2 * | 11/2002 | Bracamonte-Sommer | A61F 5/05866 602/22 |
| 7,056,298 B1 | 6/2006 | Weber | |
| 7,135,006 B1 | 11/2006 | Weber et al. | |
| 2002/0007134 A1 | 1/2002 | Bracamonte-Sommer | |
| 2003/0191421 A1 | 10/2003 | Weaver et al. | |
| 2006/0069334 A1 * | 3/2006 | Moskowitz | A61F 5/019 602/5 |
| 2010/0137769 A1 | 6/2010 | Schulte | |

* cited by examiner

*Primary Examiner* — Keri J Nelson
(74) *Attorney, Agent, or Firm* — Law Office of Scott C Harris, Inc

(57) ABSTRACT

Some embodiments of the present disclosure include a splint for resolving the symptoms of trigger finger/thumb. The splint may include a t-shaped main body, wherein a stem of the Tshape is rigid and includes a support bar configured to at least partially immobilize a user's finger and a top of the T-shape is rigid with a flexible portion configured to wrap around the finger. The splint may further include a securement strap extending from the top of the T-shape, the securement strap configured to engage with the top of the T-shape to secure the top of the Tshape around the finger. In embodiments where the splint is used on a thumb, the splint may further include a thumb securement strap configured to wrap around the user's hand/wrist to secure the splint in place.

18 Claims, 4 Drawing Sheets

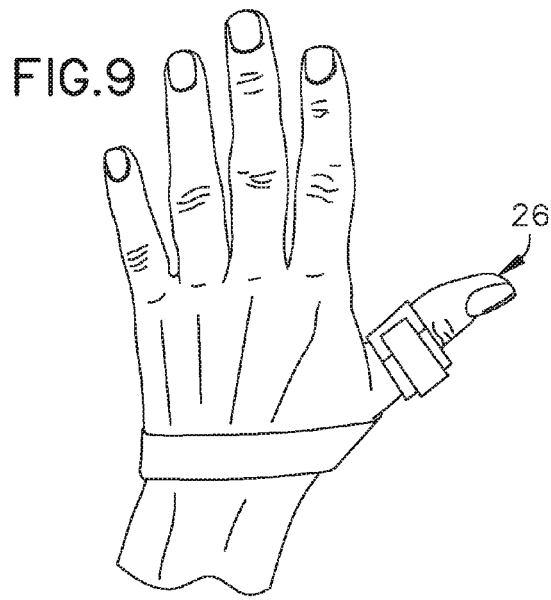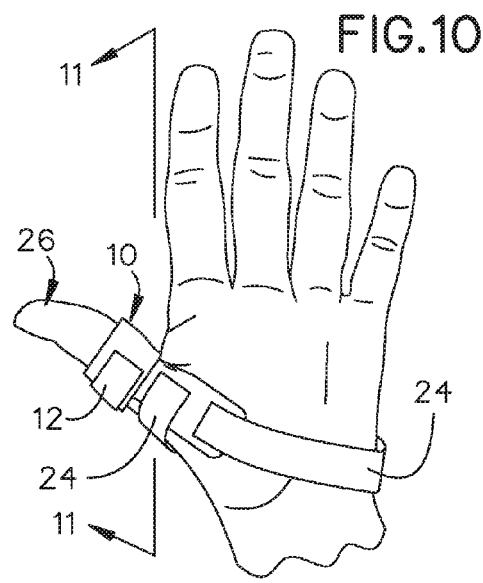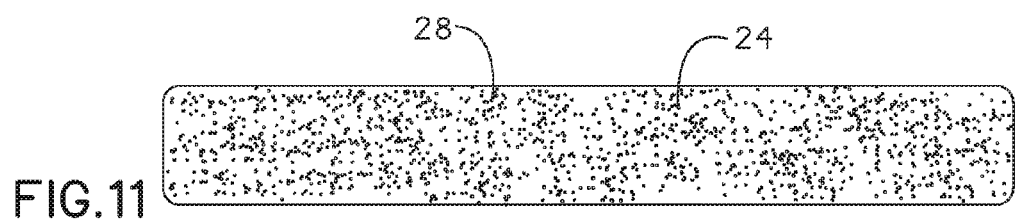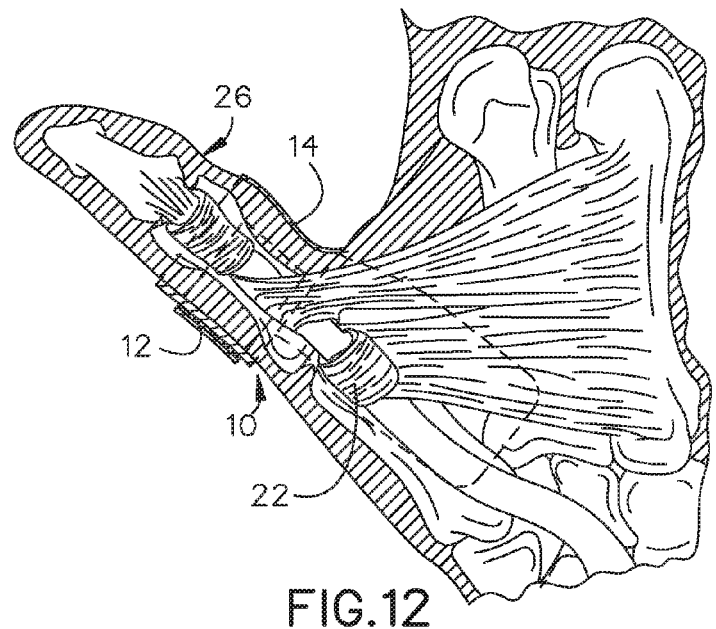

FINGER TRIGGER SPLINT FOR JOINT IMMOBILIZATION AND FLEXION INHIBITION

BACKGROUND

The embodiments herein relate generally to medical devices, and more particularly, to a finger or thumb splint to resolve the symptoms of trigger finger and thumb.

Trigger finger is a condition in which a finger (or thumb) gets stuck in a bent position. The finger may straighten out with a snap, like a trigger being pulled and released. Trigger finger occurs when inflammation narrows the space between the sheath that surrounds the tendon in the affected finger. Conventional splints for the treatment of trigger finger or trigger thumb require an orthotist or hand therapist to custom make a splint, which requires doctor's referral and is expensive. Moreover, the conventional splints are hard and uncomfortable, and people typically do not use they correctly or as suggested.

Therefore, what is needed is comfortable and effective splint for partially immobilizing a finger's flexor tendon to inhibit it from chaffing on the A1 pulley, wherein the splint is adjustable to any required size.

SUMMARY

Some embodiments of the present disclosure include a splint for resolving the symptoms of trigger finger/thumb. The splint may include a t-shaped main body, wherein a stem of the T-shape is rigid and includes a support bar configured to at least partially immobilize a user's finger and a top of the T-shape is rigid with a flexible portion configured to wrap around the finger. The splint may further include a securement strap extending from the top of the Tshape, the securement strap configured to engage with the top of the T-shape to secure the top of the T-shape around the finger. In embodiments where the splint is used on a thumb, the splint may further include a thumb securement strap configured to wrap around the user's hand/wrist to secure the splint in place.

BRIEF DESCRIPTION OF THE FIGURES

The detailed description of some embodiments of the invention is made below with reference to the accompanying figures, wherein like numerals represent corresponding parts of the figures.

FIG. 9 is a rear view of one embodiment of the present invention, shown in use.

FIG. 10 is a front view of one embodiment of the present invention, shown in use.

FIG. 11 is a rear view of one embodiment of the present invention.

FIG. 12 is a section detail view of one embodiment of the present invention, taken along line 11-11 in FIG. 10.

DETAILED DESCRIPTION OF CERTAIN EMBODIMENTS

In the following detailed description of the invention, numerous details, examples, and embodiments of the invention are described. However, it will be clear and apparent to one skilled in the art that the invention is not limited to the embodiments set forth and that the invention can be adapted for any of several applications.

The device of the present disclosure may be used to immobilize a finger joint and inhibit flexion of the finger to treat the symptoms of trigger finger and may comprise the following elements. This list of possible constituent elements is intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device.
1. Main Body
2. Support Bar
3. Securement Strap The various elements of the splint for resolving the symptoms of trigger finger of the present disclosure may be related in the following exemplary fashion. It is not intended to limit the scope or nature of the relationships between the various elements and the following examples are presented as illustrative examples only.

Figure 1:
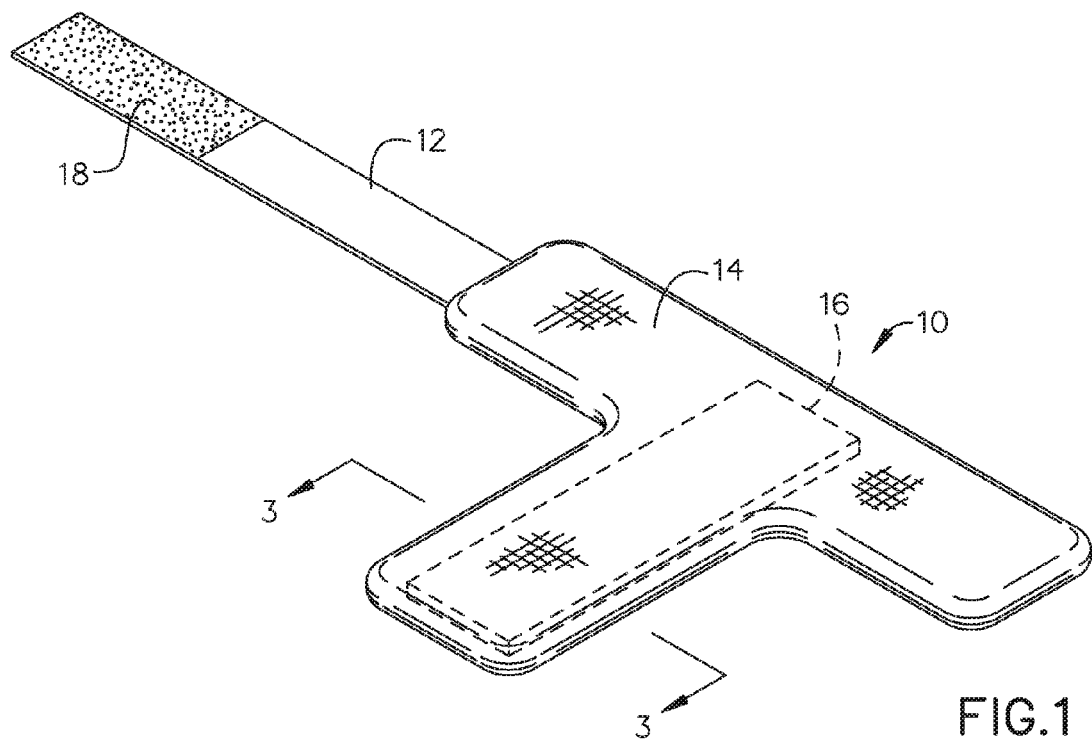
FIG. 1 is a top perspective view of one embodiment of the present invention.
Figure 2:
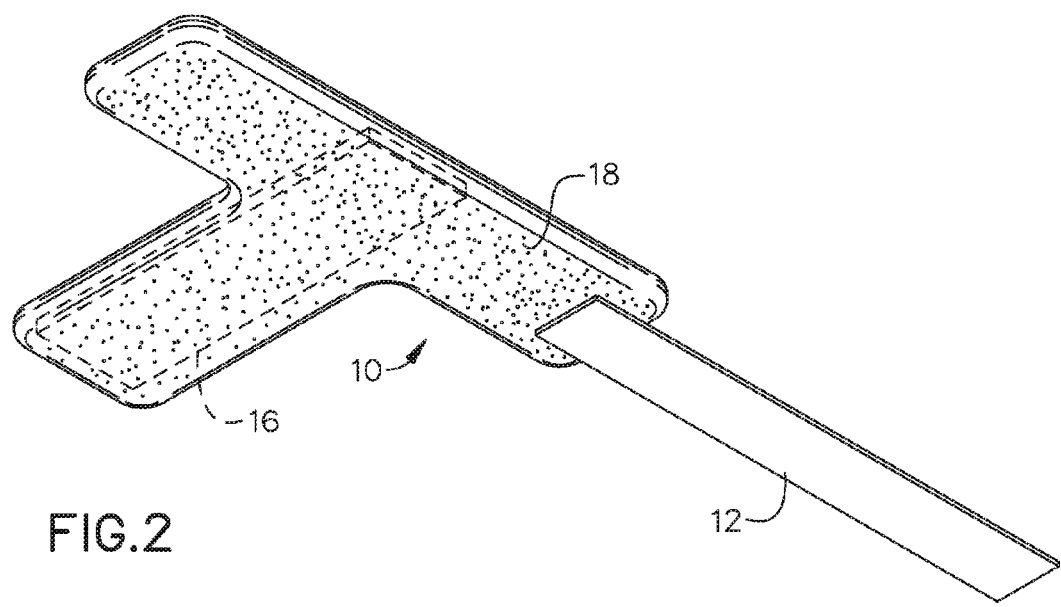
FIG. 2 is a bottom perspective view of one embodiment of the present invention.
Figure 3:
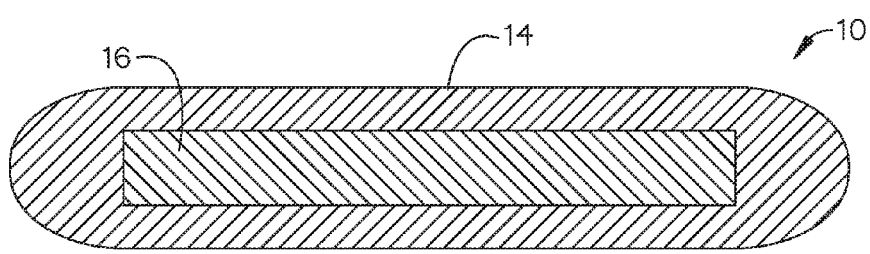
FIG. 3 is a section view of one embodiment of the present invention, taken along line 3-3 in FIG. 1.
Figure 4:
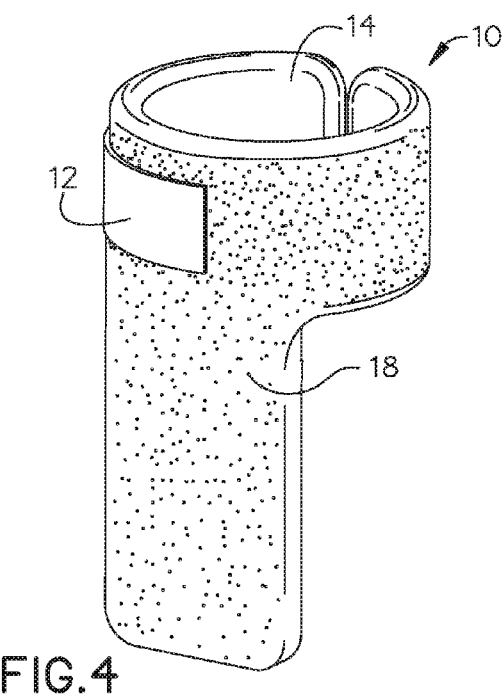
FIG. 4 is a front perspective view of one embodiment of the present invention, shown in a folded state.
Figure 5:
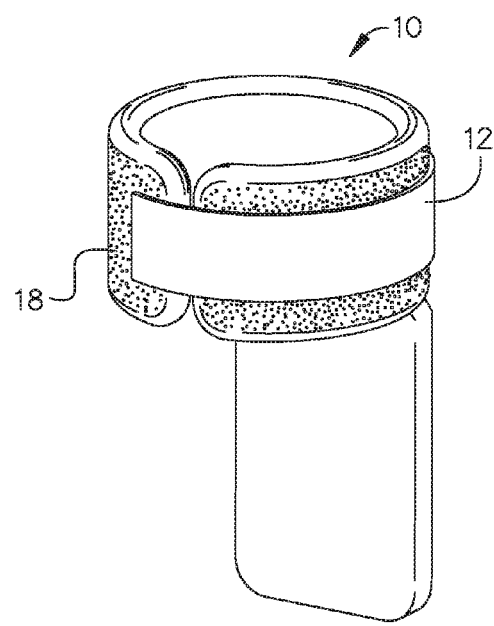
FIG. 5 is a rear perspective view of one embodiment of the present invention, shown in a folded state.

By way of example, and referring to FIGS. 1-12, some embodiments of the splint of the present disclosure comprise a main body 10 configured to align with and immobilize a metacarpophalangeal (MCP) joint in a finger 20, the main body 10 having a securement strap 12 attached thereto, wherein the main body 10 is configured to be secured to the finger 20 with the securement strap 12. In embodiments, and as shown in FIGS. 1 and 2, the main body 10 may be substantially T-shaped with the securement strap 12 extending therefrom. Specifically, the stem of the T-shape may be rigid and comprise the support bar 16, while the top of the T-shape may be rigid with a flexible portion configured to wrap around a user's finger. The main body 10 may include a support bar 16 extending through at least a portion thereof, wherein the support bar 16 is enveloped in a cushion material 14. The cushion material 14 may have a surface that is configured to be positioned opposite the user's hand, wherein the surface comprises a fastener, such as a hook and loop fastener 18. The fastener on the cushion material 14 may be configured to engage with a complementary fastener, such as a hook and loop fasteners 18, attached to at least an end portion of the securement strap 18. As shown in FIGS. 4 and 5, the main body 10 may be configured to be rolled or folded up, such that the securement strap 12 wraps around a portion of the main body 10, and the portion of the main body 10 including the support bar 16 extends from the rolled up portion.

Figure 6:
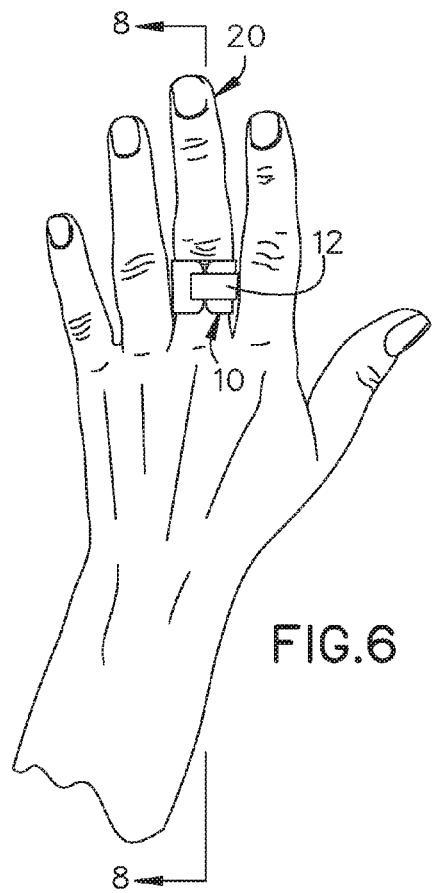
FIG. 6 is a rear view of one embodiment of the present invention, shown in use.
Figure 7:
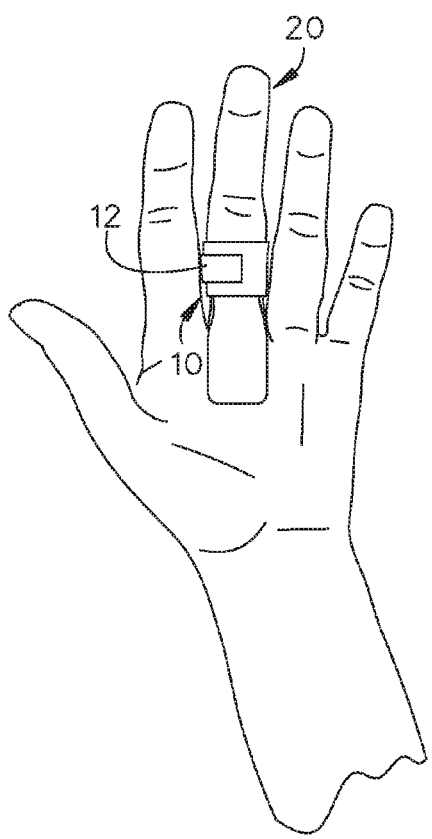
FIG. 7 is a front view of one embodiment of the present invention, shown in use.
Figure 8:
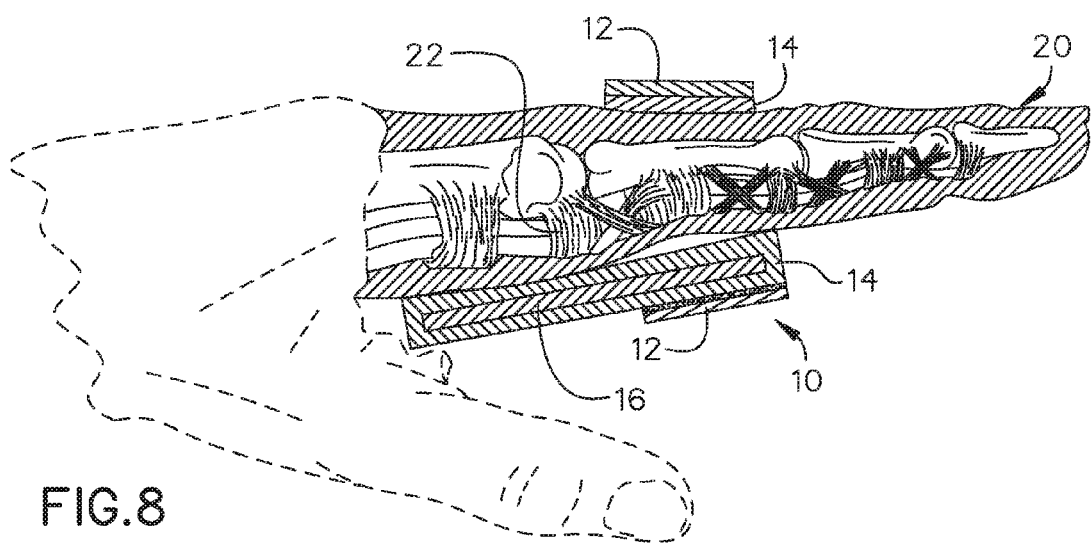
FIG. 8 is a section/cutaway detail view of one embodiment of the present invention, taken along line 8-8 in FIG. 6.

As shown in FIGS. 6-8, the splint may be positioned on a user's finger 20, such that the support bar 16 extends down the finger 20 towards the user's palm, immobilizing the MCP joint to prevent composite flexion. Because the flexor tendon is also immobilized, it is inhibited from being chaffed on the A1 pulley 22, as shown in FIG. 8.

When a user's thumb 26 is affected by trigger thumb 26, the splint may also be used to resolve the symptoms of trigger thumb. As shown in FIGS. 9-12, the splint may be placed on a user's thumb 26, such that the support bar 16 extends down the thumb 26 towards the palm and the main body 10 is wrapped around the thumb 26, secured in place using the securement strap 12. A second strap, a thumb securement strap 24 may removably engage with the main body 10, such that the thumb securement strap 24 wraps around the user's palm and wrist, securing the splint in place. As with the securement strap 12, the thumb securements strap 24 may have a surface comprising a fastener, such as a hook and loop fastener 28, configured to engage with the fastener on the main body 10.

The main body 10 may be made of any desired material. In some embodiments, the main body 10 may comprise a thermoplastic or metal support bar 16 enveloped within a fabric or cushion material 14. As mentioned above, the fasteners may comprise hook and loop fasteners, although any other desired fasteners may be used. The straps 12, 24 may comprise any suitable material, include elasticized or non elasticized materials. Because of the combination of materials used, the splint may be comfortable, effective, and adjustable to any size.

Trigger finger or thumb may be caused by a nodule forming on a tendon as a result of the tendon gliding and getting caught on the ligament. When the splint of the present disclosure is used, it may temporarily immobilize the user's finger, allowing the nodule to heal, resolving the symptoms of trigger finger or thumb.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A splint device, comprising:
A main body of a T shape, said main body formed of a stem extending along a first axis,
said main body having a first and second oppositely extending arms, each arm integral with and extending along a second axis perpendicular to said first axis, the first and second arms and the stem being integral with one another and forming the T shape,
The main body having first and second oppositely-facing surfaces,
A securement strap, attached to said first surface of the main body, and extending along said second axis,
Said securement strap having first and second oppositely-facing surfaces and having hook and loop material on said first surface of the securement strap, which faces in a first direction,
And said main body having hook and loop material on said second surface of said main body, which faces in a second direction, away from said first direction,
And where said first surface of said main body has no hook and loop material thereon,
And
Said main body and said securement strap formed of a flexible material, said main body also formed of a cushioned material, and
Said main body having a support bar of a rigid material enveloped by the cushioned material so that both a top and a bottom of the cushioned material covers the support bar, the support bar extending along the first axis
And where the stem of the main body is rigid, and the first and second arms have a flexible portion configured to wrap around a user's finger to hold the user's finger along the rigid stem, where the first and second oppositely extending arms and the securement strap curve into a generally cylindrical shape to hold a user's finger, and the stem of the main body stays rigid along said support bar and does not curve, and where the hook and loop fastener on the support arm engages with the fastener on the second surface of the main body.

2. The splint device as in claim 1, wherein the stem being in a middle of the first and second arms, and where the stem, first arm and second arm are formed from a single piece of material.

3. The splint device as in claim 1, wherein said support bar is rectangular in cross section and an area of the rectangular cross section around the support bar on the stem forms a flat section when rolled, and the arms roll into the cylindrical shape.

4. The splint device as in claim 1, wherein said main body includes bevels at edges, said bevels defining a perimeter of the T shape and where the bevels come together and touch one another when the flat section is rolled.

5. The splint device as in claim 4, wherein said bevels are rounded edge surfaces.

6. The splint device as in claim 1, wherein said securement strap is smooth and has no hook and loop material on either surface of a first section of the securement strap that is attached to the first arm, and there is hook and loop material on a second section of said arm spaced away from said first section, leaving a section of said arm where there is no hook and loop material on either surface.

7. The splint device as in claim 6, wherein said hook and loop material is on said first surface of said second section of said securement strap only, and is not on said second surface of said securement strap and is not on either said first surface or said second surface of said securement strap.

8. The splint device as in claim 1, wherein the support bar is formed of metal covered and encapsulated by the cushioned material and is not removable from the cushioned material.

9. A splint device, comprising:
A main body,
Said main body having a rolled portion at a top part that is rolled to define a cylindrical inner area at said top part,
Said cylindrical inner area defined by first and second arms rolled toward one another forming the cylindrical inner area from an inner surface of first and second arms that extend from said main body, and said first and second arms having first and second distal ends which are held to one another by a hook and loop closure material to close the cylindrical inner area, and the first and second distal ends being separable from one another,
The cylindrical inner area formed between a top surface of said first and second arms and a bottom surface of said first and second arms, where the top surface of the cylindrical inner area forms part of an outer perimeter of the main body said main body having a third portion, between the first and second arms, said third portion extending perpendicular to the first and second arms, and extending from said top surface of said first and second arms to a second area below said bottom surface of said first and second arms, along an axis, The main body having first and second oppositely-facing surfaces, A securement strap, attached to said first surface of the main body, and holding said first and second arms to one another to hold closed the cylindrical inner area, Said securement strap having first and second oppositely-facing surfaces and having hook and loop material on said first surface of said securement strap, And said main body having hook and loop material on said second surface of the main body, holding to said hook and loop material on said first surface of the main body, And Said third portion having a support bar of a rigid flat material enveloped by a cushioned material extending along said axis, where both a top and a bottom of the cushioned material cover the support bar, and the support bar extends along said axis and where said support bar forms a flattened portion as one side of the cylindrical inner area, and extending along the support bar.

10. The splint device as in claim 9, wherein said support bar is rectangular in cross section.

11. The splint device as in claim 9, wherein said main body includes bevels at its edges defining a perimeter of the main body including at least a bevel at said top surface and a bevel at the bottom surface and where the bevels come together and touch one another at edges of the cylindrical inner area.

12. The splint device as in claim 11, wherein said bevels are rounded edge surfaces.

13. The splint device as in claim 9, wherein said securement strap is smooth and has no hook and loop material on either surface of a first section of the securement strap that is attached to the first arm, and there is hook and loop material on a second section of said arm spaced away from said first section, leaving a section of said arm where there is no hook and loop material on either surface.

14. The splint device as in claim 9, wherein said main body and said first and second arms are formed of a single continuous piece of material.

15. A splint device, comprising:
a splint body, defining a cylindrical inner area which has a flattened portion along one surface of the cylindrical inner area, said cylindrical inner area being sized to fit over a human finger,
a support bar element sized to extend away from the human finger toward a palm of the hand when the splint body is fit over the human finger,
a location of the support bar element defining the flat portion,
said cylindrical inner area defined by first and second arms rolled toward one another forming the cylindrical inner area from an inner surface of said first and second arms, and said first and second arms having distal ends which are held to one another by a hook and loop closure material to close the cylindrical inner area, and the first and second ends being separable from one another to remove the splint body from the finger,
a structure forming said cylindrical inner area formed between a top surface and a bottom surface,
said support bar element extending along an axis from the finger toward the palm,
The cylindrical inner area having first and second oppositely-facing surfaces,
A securement strap, attached to said first surface of the cylindrical inner area, and holding said first and second arms to one another to form the cylindrical inner area,
Said securement strap having first and second oppositely-facing surfaces and having hook and loop material on said first surface of the securement strap,
And the structure forming said cylindrical inner area having hook and loop material on said second surface, holding to said hook and loop material on said first surface,
And
Said support bar element formed of a support bar of a rigid material enveloped by a cushioned material extending along said axis, where both a top and a bottom of the cushioned material cover the support bar, and the support bar extends along said axis.

16. The splint device as in claim 15, wherein the first and second arms along with a stem section of the splint body collectively form a T shaped structure, and where the stem, first arm and second arm are formed from a single piece of material.

17. The splint device as in claim 15, wherein said main body includes bevels at edges, said bevels defining a perimeter of the main body and where the bevels come together and touch one another at edges defining a perimeter of the cylindrical inner area.

18. The splint device as in claim 15, wherein said securement strap is smooth and has no hook and loop material on either surface of a first section of the securement strap that is attached to the first arm, and there is hook and loop material on a second section of said arm spaced away from said first section, leaving a section of said arm where there is no hook and loop material on either surface.

* * * * *